US006255563B1

(12) United States Patent
Emmermann et al.

(10) Patent No.: US 6,255,563 B1
(45) Date of Patent: Jul. 3, 2001

(54) NUCLEIC ACID MOLECULES CODING FOR DEBRANCHING ENZYMES FROM POTATO

(75) Inventors: Michael Emmermann, Bergholz-Rehbrücke; Jens Kossmann, Golm, both of (DE)

(73) Assignee: PlantTec Biotechnologie GmbH, Potsdam (DE)

( * ) Notice: Subject to any disclaimer, the term of this patent is extended or adjusted under 35 U.S.C. 154(b) by 0 days.

(21) Appl. No.: 09/187,124

(22) Filed: Nov. 5, 1998

Related U.S. Application Data

(63) Continuation of application No. PCT/EP97/02292, filed on May 6, 1997.

(30) Foreign Application Priority Data

May 6, 1996 (DE) ............................................... 196 18 125

(51) Int. Cl.$^7$ .............................. C12N 15/29; C12N 5/04; C12N 15/82; C12P 19/04; A01H 5/00
(52) U.S. Cl. ...................... 800/284; 800/317.2; 800/320; 800/320.1; 435/69.1; 435/101; 435/252.3; 435/320.1; 435/412; 435/417; 435/419; 536/23.6
(58) Field of Search ......................... 536/23.6; 435/69.1, 435/101, 252.3, 320.1, 419, 412, 417; 800/284, 317.2, 320, 320.1

(56) References Cited

U.S. PATENT DOCUMENTS

| 4,454,161 | 6/1984 | Okada et al. ............................ 426/48 |
| 6,001,628 | 12/1999 | Kossmann et al. ................... 435/210 |
| 6,057,493 | 5/2000 | Willmitzer et al. .................. 800/284 |
| 6,066,782 | 5/2000 | Kossmann et al. ................... 800/284 |
| 6,117,665 | 9/2000 | Kossmann et al. ................... 435/210 |

FOREIGN PATENT DOCUMENTS

| 19028/95 | 10/1995 | (AU) . |
| 0 479 359 A1 | 4/1992 | (EP) . |
| 0 529 894 A1 | 3/1993 | (EP) . |
| 0 554 122 A1 | 8/1993 | (EP) . |
| WO 92/11376 | 7/1992 | (WO) . |
| WO 92/11382 | 7/1992 | (WO) ............................. C12P/21/00 |
| WO 92/14827 | 9/1992 | (WO) . |
| WO 95/04826 | 2/1995 | (WO) ............................. C12N/15/56 |
| WO 95/09922 | 4/1995 | (WO) . |
| WO 96/03513 | 2/1996 | (WO) ............................. C12N/15/55 |
| WO 96/19581 | 6/1996 | (WO) ............................. C12N/15/56 |

OTHER PUBLICATIONS

Doehlert et al. J. Plant Physiol. 138:566–572 1991.*
Hannah et al. Scientia Hortic. 55: 177–197, 1993.*
Kossmann et al. Progress Biotechnol. 10:271–278, 1995.*
Black, R.C. et al., "Genetic Interactions Affecting Maize Phytoglycogen and the Phytoglycogen–Forming Branching Enzyme", *Genetics*, 53, 661–668 (1966).

Hawker, J.S. et al., "Interaction of Spinach Leaf Adenosine Diphosphate Glucose α–1,4–Glucan α4–Glucosyl Transferase and α–1,4–Glucan, α1,4–Glucan–6–Glycosyl Transferase in Synthesis of Branched α–Glucan", *Archives of Biochemistry and Biophysics*, 160, 530–551 (1974).
Hobson, P.N. et al., "The Enzymic Synthesis and Degradation of Starch—Part XIV—R–Enzyme", *Journal of the Chemical Society*, 1451–1459 (1951).
Katsuragi, N. et al., "Entire Nucleotide Sequence of the Pullulanse Gene of *Klebsiella aerogenes* W70", *Journal of Bacteriology*, 169, 2301–2306 (1987).
Li, B. et al., "Characterization and Subcellular Localization of Debranching Enzyme and Endoamylase from Leaves of Sugar Beet", *Plant Physiology*, 98, 1277–1284 (1992).
Ludwig, Isabella et al., "Purification and Properties of Spinach Leaf Debranching Enzyme", *Plant Physiology*, 74, 856–861 (1984).
Manners, D.J. et al., "Studies on Carbohydrate–Metabolising Enzymes: Part XX. Sweet Corn Debranching Enzymes", *Carbohyd. Res.*, 9, 107–121 (1969).
Pan, D. et al., "A Debranching Enzyme Deficiency in Endosperms of the Sugary–1 Mutants of Maize", *Plant Physiol.*, 74, 324–328 (1984).
Renz, A. et al., "S.oleracea L. mRNA for Pullulanse", EMBL Sequence Database, Accession No. X83969 (1995).
Schaller, A., "The Electronic Plant Gene Register", Plant Physiology, 108, 1341–1343 (1995).
Shannon, J.C. et al., "Genetics and Physiology of Starch Development", *Starch: Chemistry and Technology*, 2d Ed., 25–86 (1984).
Visser, R.G.F. et al., "Inhibition of the expression of the gene for granule–bound starch synthase in potato by antisense constructs", *Mol. Gen. Genet.*, 225, 289–296 (1991).
Y. Ishizaki et al., "Debranching Enzymes of Potato Tubers (*Solanum tuberosum* L.). I. Purification and Some Properties of Potato Isoamylase," *Agric. Biol. Chem.*, 47(4), pp. 771–779 (1983).
Y. Ishizaki et al., "Debranching Enzymes of Potato Tubers (*Solanum tuberosum* L.). II. Purification of a Pullulanase (R–enzyme) from Potato Tubers and Comparison of its Properties with Those of the Potato Isoamylase," *Chemical Abstracts*, 99(9), pp. 273 (1983).
M.G. James et al., "Characterization of the Maize Gene sugary1, a Determinant of Starch Composition in Kernels," *The Plant Cell*, 7, pp. 417–429 (1995).

* cited by examiner

*Primary Examiner*—David T. Fox
(74) *Attorney, Agent, or Firm*—Fish & Neave; James F. Haley, Jr.; Li Su

(57) ABSTRACT

Nucleic acid molecules are described, which encode debranching enzymes from potato, as well as transgenic plant cells and plants in which an amylopectin with modified properties is synthesized due to the expression of a debranching enzyme from potato or due to the inhibition of such an endogeneous debranching enzyme activity.

28 Claims, No Drawings

NUCLEIC ACID MOLECULES CODING FOR DEBRANCHING ENZYMES FROM POTATO

This application is a continuation of international application PCT/EP97/02292, filed on May 6, 1997, which designated the United States.

FIELD OF THE INVENTION

Nucleic acid molecules coding for debranching enzymes from potato The present invention relates to nucleic acid molecules encoding proteins from potato with the enzymatic activity of a debranching enzyme. The invention further relates to transgenic plants and plant cells, in which an amylopectin with an altered degree of branching is synthesized due to the expression of an additional debranching enzyme activity from potato or due to the inhibition of an endogeneous debranching enzyme activity. The invention also relates to the starch obtainable from said transgenic plant cells and plants.

Starch plays an important role as storage substance in a multitude of plants and also as a regenerative, industrially usable raw material and has gained increasing significance. For the industrial use of starch it is necessary that it meets the demands of the processing industry with respect to its structure, form and/or other physico-chemical parameters. In order to enable the use in as many areas as possible it is furthermore necessary to achieve a large variety of substances. The polysaccharide starch is made up of chemically homogeneous basic components, namely the glucose molecules. However, it constitutes a highly complex mixture of various types of molecules which differ from each other in their degree of polymerization and in the degree of branching. One differentiates between amylose-starch, a basically non-branched polymer made up of $\alpha$-1,4-glycosidically branched glucose molecules, and amylopectin-starch, a branched polymer, in which the branching results from additional $\alpha$-1,6-glycosidic interlinkings.

In plants used typically for the production of starch, such as maize or potato, the synthesized starch consists of approximately 25% amylose-starch and of about 75% amylopectin-starch. In the case of maize, for example, a further branched polysaccharide, apart from amylopectin, occurs, namely the so-called phytoglycogen which differs from amylopectin by exhibiting a higher degree of branching and different solubility (see e.g. Lee et al., Arch. Biochem. Biophys. 143 (1971), 365–374; Pan and Nelson, Plant Physiol. 74 (1984), 324–328). In the scope of the present application the term amylopectin is used in such a way as to comprise the phytoglycogen.

With respect to the homogeneity of the basic component starch for its use in the industrial area, starch-producing plants are needed which contain, for example, only the component amylopectin or only the component amylose. For a number of other uses plants are needed that synthesize amylopectin types with different degrees of branchings.

Such plants may for example be obtained by breeding or by means of mutagenesis techniques. It is known for various plant species, such as for maize, that by means of mutagenesis varieties may be produced in which only amylopectin is formed. Also in the case of potato a genotype was produced from a haploid line by means of chemical mutagenesis. Said genotype does not form amylose (Hovenkamp-Hermelink, Theor. Appl. Genet. 75 (1987), 217–221).

Apart from conventional breeding and mutagenesis techniques, recombinant DNA techniques are now increasingly used in order to specifically interfere with the starch metabolism of starch storing plants. A prerequisite for this is that DNA sequences be provided which encode enzymes involved in the starch metabolism. In the case of potato, for example, DNA sequences have by now been found which encode a granule-bound starch synthase or a branching enzyme (Q enzyme), and they have been used in order to genetically modify plants.

For a further targeted modification of the starch in plants, in particular of the degree of branching of starch synthesized in plants by means of recombinant DNA techniques, it is still necessary to identify DNA sequences that encode enzymes participating in the starch metabolism, particularly in the branching of starch molecules.

Apart from the Q enzymes that introduce branchings into starch molecules, enzymes occur in plants which are capable of dissolving branchings. These enzymes are called debranching enzymes.

In the case of sugar beet, Li et al. (Plant Physiol. 98 (1992), 1277–1284) could only prove the occurrence of one debranching enzyme, apart from five endo- and two exoamylases. This enzyme having a size of approximately 100 kD and an optimum pH value of 5.5 is located within the chloroplasts. A debranching enzyme was also described for spinach. The debranching enzyme from spinach as well as that from sugar beet exhibit a fivefold lower activity in a reaction with amylopectin as substrate when compared to a reaction with pullulan as a substrate (Ludwig et al., Plant Physiol. 74 (1984), 856–861; Li et al., Plant Physiol. 98 (1992), 1277–1284). The isolation of a cDNA encoding a debranching enzyme was described for spinach (Renz et al., Plant Physiol. 108 (1995), 1342).

The existence of a debranching enzyme for maize has been described in the prior art. The corresponding mutant was designated su (sugary). The gene of the sugary locus was cloned recently (see James et al., Plant Cell 7 (1995), 417–429). In the case of the agriculturally significant starch-storing cultured plant potato, the activity of a debranching enzyme was examined by Hobson et al. (J. Chem. Soc., (1951), 1451). It was proven that the respective enzyme, contrary to the Q enzyme, does not exhibit any activities leading to an elongation of the polysaccharide chain, but merely hydrolyses $\alpha$-1,6-glycosidic bonds. Methods for the purification of a debranching enzyme from potato as well as partial peptide sequences of the purified protein have already been described (WO 95/04826).

So far no indication as to the existence of further debranching enzyme types from potato could be found. Should this, however, be the case, all debranching enzyme types occurring in potato would have to be identified and the corresponding genes or cDNA sequences would have to be isolated in order to produce transgenic potato plants that do no longer exhibit any debranching enzyme activity for the purpose of achieving a modification of the degree of branching of the amylopectin starch.

Therefore, the technical problem underlying the present invention is to identify further debranching enzymes possibly occurring in potato and to isolate corresponding nucleic acid molecules encoding these enzymes.

This problem is solved by the provision of the embodiments as defined in the claims.

SUMMARY OF THE INVENTION

Thus, the present invention relates to nucleic acid molecules encoding proteins with the biological activity of a debranching enzyme from potato. Such a nucleic acid molecule preferably encodes a protein with the biological activity of a debranching enzyme from potato that exhibits the amino acid sequence depicted in SEQ ID No. 2. In a particularly preferred embodiment such a nucleic acid molecule comprises the nucleotide sequence depicted under SEQ ID No. 1, in particular the coding region.

The present invention also relates to nucleic acid molecules encoding proteins with the biological activity of a debranching enzyme from potato and hybridizing to one of the above-described nucleic acid molecules or to the complementary strand thereof. Furthermore, the present invention relates to nucleic acid molecules the sequence of which differs from the sequences of the above-mentioned nucleic acid molecules due to a degeneracy of the genetic code, and which encode a protein exhibiting the biological activity of a debranching enzyme from potato.

The term "from potato" means that the debranching enzymes encoded by the nucleic acid molecules of the invention are typical for the species Solanum tuberosum, i.e. they either occur naturally in such plants, for example encoded by genomic or RNA molecules or by molecules derived therefrom. Derived molecules may for example be produced by the reverse transcription of RNA molecules, amplification, mutation, deletion, substitution, insertion etc. I.e. the term also comprises enzymes encoded by alleles and derivatives of sequences naturally occurring in potato. These may for example be produced by in vitro by means of recombinant DNA techniques.

DETAILED DESCRIPTION OF THE INVENTION

In the scope of the present invention the term "hybridization" signifies hybridization under conventional hybridizing conditions, preferably under stringent conditions, as described for example in Sambrook et al., Molecular Cloning, A Laboratory Manual, 2nd Edition (1989) Cold Spring Harbor Laboratory Press, Cold Spring Harbor, N.Y.). Nucleic acid molecules hybridizing to the nucleic acid molecules of the invention may basically be derived from any desired type of potato plant. Nucleic acid molecules hybridizing to the molecules of the invention may for example be isolated from genomic or cDNA libraries.

The identification and isolation of such nucleic acid molecules may take place by using the molecules of the invention or parts of these molecules or, as the case may be, the reverse complements of these molecules, e.g. by hybridization according to standard methods (see e.g. Sambrook et al., 1989, Molecular Cloning, A Laboratory Manual, 2nd Edition, Cold Spring Harbor Laboratory Press, Cold Spring Harbor, N.Y.) or by means of amplification via PCR.

As a probe for hybridization e.g. nucleic acid molecules may be used which exactly or basically contain the nucleotide sequence indicated under Seq ID No. 1 or parts thereof. The fragments used as hybridization probe may also be synthetic fragments which were produced by means of the conventional synthesizing methods and the sequence of which is basically identical to that of a nucleic acid molecule of the invention. After identifying and isolating the genes hybridizing to the nucleic acid sequences of the invention, the sequence has to be determined and the properties of the proteins encoded by this sequence have to be analyzed.

The molecules hybridizing to the nucleic acid molecules of the invention also comprise fragments, derivatives and allelic variants of the above-described DNA molecules which encode a protein with the enzymatic activity of a debranching enzyme from potato or a biologically, i.e. enzymatically active fragment thereof. In this context, fragments are defined as parts of the nucleic acid molecules, which are long enough in order to encode a polypeptide with the enzymatic activity of a debranching enzyme. In this context, the term derivative means that the sequences of these molecules differ from the sequences of the above-mentioned nucleic acid molecules at one or more positions and that they exhibit a high degree of homology to these sequences. In this regard, homology means a sequence identity of at least 70%, in particular an identity of at least 80%, preferably of more than 90% and still more preferably a sequence identity of more than 95%. The deviations occurring when compared to the above-described nucleic acid molecules might have been caused by deletion, addition, substitution, insertion or recombination.

Moreover, homology means that the respective nucleic acid molecules or the proteins they encode are functionally and/or structurally equivalent. The nucleic acid molecules which are homologous to the above-described molecules and represent derivatives of these molecules, are generally variations of these molecules that constitute modifications exerting the same biological function. These variations may be naturally occurring variations, for example sequences derived from other potato plants or varieties, or mutations, wherein these mutations may have occurred naturally or they may have been introduced by means of a specific mutagenesis. Moreover, the variations may be synthetically produced sequences. The allelic variants may be naturally occurring as well as synthetically produced variants or variants produced by recombinant DNA techniques.

The proteins encoded by the various variants of the nucleic acid molecules according to the invention exhibit certain common characteristics. Enzyme activity, molecular weight, immunologic reactivity, conformation etc. may belong to these characteristics as well as physical properties such as the mobility in gel electrophoresis, chromatographic characteristics, sedimentation coefficients, solubility, spectroscopic properties, stability; pH-optimum, temperature-optimum etc.

The enzymatic activity of the debranching enzyme may for example be shown by means of a staining test, as described in WO 95/04826. This test is based on the fact that a protein with a starch-modifying activity may be shown by separating protein extracts, for example from potato tubers, in non-denaturing amylopectin- containing polyacrylamide gels (PMG) and the gel is subsequently, after incubation with a suitable buffer, subjected to iodine staining. While unbranched amylose treated with iodine shows a blue staining, amylopectine exhibits a reddish purple staining. In amylopectin-containing polyacrylamide gels which turn reddish purple when treated with iodine, the color of the gel tends to turn into blue at positions where a debranching activity is localized, since the branchings of the purple-staining amylopectin are dissolved by the debranching enzyme.

Alternatively, the debranching enzyme activity may be shown by means of the DNSS test (see Ludwig et al., Plant Physiol. 74 (1984), 856–861).

The nucleic acid molecules of the invention may be any desired nucleic acid molecules, in particular DNA or RNA molecules, such as cDNA, genomic DNA, mRNA etc. They may be naturally occurring molecules or they may be produced by means of recombinant DNA or chemical synthesizing techniques.

The nucleic acid molecules according to the present invention encode a so far unknown protein from potato with the enzymatic activity of a debranching enzyme. So far only one debranching enzyme had been described for potato. There was no indication in the prior art that genes exist in potato encoding further debranching enzymes. Now it was surprisingly found that, apart from the debranching enzyme from potato known so far, at least one further enzyme with debranching activity exists. Thus, the molecules of the invention encode a novel type of debranching enzymes from potato. By means of these molecules it is now possible to specifically interfere with the starch metabolism of potato and other starch-storing plants and, thus, to enable the synthesis of a starch modified in its chemical or physical properties. This may be carried out by over-expressing the nucleic acid molecules of the invention in any desired, preferably starch-storing plants or by reducing the debranching enzyme activity in potato plants by making use of the nucleic acid sequences of the invention, for example by antisense or ribozyme effects.

Furthermore, the present invention relates to nucleic acid molecules with a length of at least 15, preferably of more than 50 and most preferably of more than 200 base pairs, which specifically hybridize to the nucleic acid molecules of the invention. In this context, specifically hybridizing means that these molecules hybridize to nucleic acid molecules encoding the novel debranching enzymes from potato, however, not to nucleic acid molecules encoding other proteins. In this regard, hybridizing preferably means hybridization under stringent conditions (see above). The invention particularly relates to such nucleic acid molecules that hybridize to transcripts of the nucleic acid molecules of the invention, thereby preventing their translation. Such nucleic acid molecules specifically hybridizing with the nucleic acid molecules of the invention may for example be parts of mRNA constructs or ribozymes or may be used as primers for the amplification by means of PCR.

Furthermore, the invention relates to vectors, especially plasmids, cosmids, viruses, bacteriophages and other vectors common in genetic engineering, which contain the above-mentioned nucleic acid molecules of the invention.

In a preferred embodiment the nucleic acid molecules contained in the vectors are linked to regulatory elements that ensure the transcription and translation in prokaryotic or eukaryotic cells.

In a further embodiment the invention relates to host cells, in particular prokaryotic or eukaryotic cells, which have been transformed by an above-mentioned nucleic acid molecule or vector, as well as to cells derived from such host cells and containing the described nucleic acid molecules or vectors. The host cells may be bacterial or fungal cells, as well as plant or animal cells.

The invention also relates to proteins with the biological activity of a debranching enzyme from potato which are encoded by the nucleic acid molecules of the invention, or to biologically active fragments thereof.

Furthermore, the present invention relates to methods for the production of a protein with the biological activity of a debranching enzyme from potato or a biologically active fragment thereof, wherein host cells of the invention are cultivated under suitable conditions and wherein the protein is isolated from the culture, i.e. from the cells and/or the culture medium.

In a preferred embodiment the host cells of the invention are transgenic plant cells which due to the presence and expression of an introduced nucleic acid molecule of the invention either exhibit a novel or an increased debranching enzyme activity when compared to untransformed cells.

By the provision of the nucleic acid molecules according to the present invention it is now possible to modify plant cells by means of recombinant DNA techniques in such a way that they exhibit a novel or increased debranching enzyme activity when compared to wildtype cells.

Such transgenic plant cells differ from untransformed cells in that the introduced nucleic acid molecule is either heterologous to the transformed cell, i.e. derived from a cell with a different genomic background, or in that the introduced nucleic acid molecule, if it is homologous to transformed plant species, is localized at a position in the genome where it does not naturally occur in non-transformed cells. The introduced nucleic acid molecule may either be subjected to the control of its natural promoter or be linked with regulatory elements of foreign genes.

Transgenic plants containing the above-described transgenic plant cells are also the subject matter of the present invention.

The plant which is transformed with the nucleic acid molecules of the invention and in which a debranching enzyme from potato is synthesized due to the introduction of such a molecule may principally be any desired kind of plant. It is preferably a monocotyledonous or dicotyledonous useful plant, in particular a starch storing plant, such as cereals, Leguminosae, potatoes or cassava.

The cereals are in particular monocotyledonous plants belonging to the Poales order, in particular of the family of the Poaceae. Examples thereof are plants belonging to the genuses Avena (oats), Triticum (wheat), Secale (rye), Hordeum (barley), Oryza (rice), Panicum, Pennisetum, Setaria, Sorghum (millet), Zea (maize) etc. Starch-storing Leguminosae are e.g. some types of the genus Pisum (e.g. Pisum sativum), Vicia (e.g. Vicia faba), Cicer (e.g. Cicer arietinum), Lens (e.g. Lens culinaris), Phaseolus (e.g. Phaseolus vulgaris and Phaseolus coccineus), etc.

The present invention also relates to starch obtainable from the transgenic plant cells or plants. The expression of a novel or additional debranching enzyme activity from potato in the transgenic plant cells and plants of the invention influences the degree of branching of the amylopectin synthesized in the cells and plants. Therefore, a starch synthesized in these plants exhibits modified physical and/or chemical properties when compared to starch from wildtype plants.

Furthermore, the present invention relates to propagation material of the transgenic plants of the invention, such as seeds, fruits, cuttings, tubers, rootstocks etc., wherein this propagation material contains the above-described transgenic plant cells. In the case of potato plants the propagation material are preferably tubers.

Furthermore, the present invention relates to transgenic plant cells from potato in which the activity of the debranching enzyme of the invention is reduced due to the inhibition of the transcription or translation of endogeneous nucleic acid molecules encoding a such a novel debranching enzyme. This is preferably achieved by expressing a nucleic acid molecule of the invention or a part thereof in the corresponding plant cells in antisense orientation and by the fact that due to the antisense effect the described debranching enzyme activity is reduced. A further possibility in order to reduce the debranching enzyme activity in plant cells is to express suitable ribozymes that specifically cleave transcripts of the DNA molecules of the invention. The production of such ribozymes by means of the DNA molecules of the invention is known to the skilled person. It is also possible to express molecules which exert an antisense effect in combination with a ribozyme effect. Alternatively, the debranching enzyme activity in the plant cells may be reduced by means of a cosuppression effect. This method is known to the skilled person and has e.g. been described in Jorgensen (Trends Biotechnol. 8 (1990), 340–344), Niebel et al. (Curr. Top. Microbiol. Immunol. 197 (1995), 91–103), Flavell et al. (Curr. Top. Microbiol. Immunol. 197 (1995), 43–46), Palaqui and Vaucheret (Plant. Mol. Biol. 29 (1995), 149–159), Vaucheret et al. (Mol. Gen. Genet. 248 (1995), 311–317), de Borne et al. (Mol. Gen. Genet. 243 (1994), 613–621) and other sources. The expression of ribozymes in order to reduce the activity of a particular enzyme in cells is also known to the skilled person and has for example been described in EP-B1 0 321 201. The expression of ribozymes in plant cells has for example been described by Feyter et al. (Mol. Gen. Genet. 250 (1996), 329–338). Other possibilities in order to reduce the activity of the described novel debranching enzymes in plant cells are known to the skilled person, for example mutagenesis of genomic sequences encoding such enzymes, e.g. by gene tagging or transposon mutagenesis or by expressing antibodies which specifically recognize the novel debranching enzymes. The mutagenesis of genomic sequences may apply for coding regions of the gene (introns and exons) or also to regulatory regions, in particular to those necessary for initiating transcription.

The invention further relates to transgenic potato plants containing the above-described transgenic plant cells with reduced debranching enzyme activity.

The modified starch obtainable from the transgenic cells or plants is also the subject matter of the present invention. When compared to non-transformed plants, the amylopectin starch of the transgenic cells and plants exhibits a modified degree of branching due to the reduced debranching enzyme activity.

The invention also relates to propagation material of the above-described transgenic plants, in particular to seeds and tubers, wherein said material contains the above-mentioned transgenic plant cells.

Transgenic plant cells forming an amylopectin starch with a modified degree of branching in comparison to amylopectin starch synthesized in wildtype plants due to the expression of a novel or additional debranching enzyme activity, may for example be produced by a method comprising the following steps:
 (a) Production of an expression cassette comprising the following DNA sequences:
  (i) a promoter ensuring the transcription in plant cells;
  (ii) at least one nucleic acid sequence of the invention which encodes a protein with the enzymatic activity of a debranching enzyme or a biologically active fragment thereof and which is coupled to the 3'-end of the promoter in sense-orientation; and
  (iii) optionally, a termination signal for the termination of transcription and the addition of a poly-A-tail to the developing transcript, which is coupled to the 3'-end of the coding region; and
 (b) transforming plant cells with the expression cassette produced in step (a).

Transgenic plant cells forming an amylopectin starch with a modified degree of branching in comparison to amylopectin starch synthesized in wildtype plants due to the reduction of the described debranching enzyme activity, may for example be produced by a method comprising the following steps:
 (a) Production of an expression cassette comprising the following DNA sequences:
  (i) a promoter ensuring the transcription in plant cells;
  (ii) at least one nucleic acid sequence of the invention which encodes a protein with the enzymatic activity of a debranching enzyme or a biologically active part thereof and which is coupled to the 3'-end of the promoter in antisense-orientation; and
  (iii) optionally, a termination signal for the termination of transcription and the addition of a poly-A-tail to the developing transcript, which is coupled to the 3'-end of the coding region; and
 (b) transforming plant cells with the expression cassette produced in step (a).

Basically every promoter functional in the plants selected for transformation may be used as the promoter mentioned under (i). The promoter may be homologous or heterologous with respect to the used plant species. Use may, for example, be made of the 35S promoter of the cauliflower mosaic virus (Odell et al., Nature 313 (1985), 810–812) which ensures a constitutive expression in all plant tissues and also of the promoter construct described in WO/9401571. Another example are the promoters of the polyubiquitin genes from maize (Christensen et al., Plant Mol. Biol. 18 (1992) 675–689). However, use may also be made of promoters which are only activated at a point of time determined by exogeneous factors (such . as in WO/9307279). In this regard, promoters of heat-shock proteins allowing for simple induction may be of particular interest. Furthermore, promoters may be used that lead to the expression of downstream sequences in a particular tissue of the plant (see e.g. Stockhaus et al., EMBO J. 8 (1989), 2245–2251). Promoters which are active in the starch-storing parts of the plant to be transformed are preferably used. In the case of maize these parts are the maize kernels, in the case of potatoes the tubers. In order to overexpress the nucleic acid molecules of the invention in potatoes, the tuber-specific B33-promoter (Rocha-Sosa et al., EMBO J. 8 (1989), 23–29) may for example be used.

Seed-specific promoters have already been described for various plant species, such as the USP promoter from Vicia faba which ensures a seed-specific expression in V. faba and other plants (Fiedler et al., Plant Mol. Biol. 22 (1993), 669–679; Baumlein et al., Mol. Gen. Genet. 225 (1991), 459–467). In the case of maize, for example, promoters of the zein genes ensure a specific expression within the endosperm of the maize kernels (Pedersen et al., Cell 29 (1982), 1015–1026; Quattrocchio et al., Plant Mol. Biol. 15 (1990), 81–93).

In the case that the nucleic acid sequence mentioned under process step (a)(ii), which encodes a protein with the enzymatic activity of a debranching enzyme from potato, is linked to the promoter in sense-orientation, this nucleic acid sequence may be of native or homologous origin as well as of foreign or heterologous origin with respect to the plant species to be transformed, i.e. potato plants as well as any desired other plants (preferably the above-mentioned, starch-storing plants) may be transformed with the described expression cassette.

The synthesized protein may in principle be located in any desired compartment within the plant cell. Plant debranching enzymes are generally located within the plastids and therefore possess a signal sequence for the translocation into these organelles. In order to achieve localization within another compartment, the DNA sequence encoding this signal sequence must be deleted and the coding region has to be linked to DNA sequences which ensure localization in the respective compartment. Such sequences are known (see e.g. Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

In case that the nucleic acid sequence from potato mentioned under process step (a)(ii), which encodes a protein with the enzymatic activity of a debranching enzyme, is linked to the promoter in antisense-orientation, it is preferably a nucleic acid sequence of homologous origin with respect to the plant species to be transformed. However, also nucleic acid sequences may be used which exhibit a high degree of homology to endogeneously present debranching enzyme genes, in particular homologies of more than 80%, preferably homologies of between 90% and 100% and most preferably homologies of more than 95%.

Sequences with a minimum length of 15 bp may be used. Even when using shorter sequences, an inhibiting effect cannot be excluded. Longer sequences ranging between 100 to 500 base pairs are preferably used; for an efficient antisense inhibition, sequences with a length of more than 500 base pairs are used. Usually, use is made of sequences that are shorter than 5000 base pairs, preferably sequences that are shorter than 2500 base pairs.

Termination signals for the transcription in plant cells are described and may be interchanged as desired. For example, use can be made of the termination sequence of the octopin-synthase gene from *Agrobacterium tumefaciens*.

The transfer of the expression cassette constructed according to process step (a) is preferably carried out by using plasmids, in particular by means of plasmids ensuring a stable integration of the expression cassette into the plant genome.

The above-described method for overexpressing a novel debranching enzyme from potato may principally be used for all plant species. In this context, monocotyledonous and dicotyledonous plants and in particular the above-mentioned starch-storing plants are of interest. The above-described method for reducing the debranching enzyme activity is preferably used for dicotyledonous plants, in particular for potatoes.

Due to the introduction of an expression cassette constructed according to the above-described methods, an RNA is formed within the transformed plant cells. If the nucleic acid sequence encoding a debranching enzyme from potato is linked to the promoter in sense-orientation in the expression cassette, an mRNA is synthesized which may serve as a matrix for the synthesis of an additional or novel debranching enzyme from potato in the plant cells. As a consequence thereof, these cells exhibit an activity or, as the case may be, increased activity of the debranching enzyme from potato, which leads to a modification of the degree of branching of the amylopectin formed in the cells. Thereby, a starch is made accessible which in comparison to naturally occuring starch is characterized by a more clearly ordered structure as well as by an increased homogeneity. This may, among other things, favorably influence the film forming properties.

If, however, the nucleic acid sequence encoding a debranching enzyme from potato is linked to the promoter in antisense-orientation, an antisense-RNA is synthesized within the transgenic plant cells inhibiting the expression of endogeneous debranching enzyme genes. As a consequence, these cells exhibit a reduced activity of the novel debranching enzyme from potato, which leads to the synthesis of a modified starch. By means of the antisense technique it is possible to produce plants in which the expression of an endogeneous debranching enzyme gene in potato is inhibited to different degrees within the range of 0% to 100%. This enables in particular the production of potato plants synthesizing amylopectin starch with most various variations of the degree of branching. This constitutes an advantage with regard to conventional breeding and mutagenesis techniques in which a lot of time and costs are required in order to provide such a variety. Highly branched amylopec-tin has a particularly large surface and is therefore particularly suitable as a copolymer. A high degree of branching furthermore leads to an improvement of the amylopectin's solubility in water. This property is very advantageous for certain technical applications.

Potato is particularly suitable for the production of modified amylopectin by using the nucleic acid molecules of the invention encoding debranching enzymes. The application of the invention is, however, not limited to this plant species. Any desired other plant species may be used for overexpression.

The modified starch synthesized in the transgenic plants may be isolated from the plants or from the plant cells by means of conventional methods and may be used for the production of foodstuffs and industrial products after purification.

The starch according to the invention can be modified by the person skilled in the art by known methods and can be used in modified or unmodified form for different uses in the food or non-food industry.

Basically, the uses of starch can be subdivided into two major fields. One field comprises the hydrolysis products of starch and the so-called native starches. The hydrolysis products essentially comprise glucose and glucans components obtained by enzymatic or chemical processes. They can be used for further processes, such as fermentation and chemical modifications. In this context, it might be of importance that the hydrolysis process can be carried out simply and inexpensively. Currently, it is carried out substantially enzymatically using amyloglucosidase. It is thinkable that costs might be reduced by using lower amounts of enzymes for hydrolysis due to changes in the starch structure, e.g. increasing the surface of the grain, improved digestibility due to less branching or a steric structure, which limits the accessibility for the used enzymes.

The use of the so-called native starch which is used because of its polymer structure can be subdivided into two further areas:

1. Use in Foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

2. Use in Non-Foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized. 2.1 Paper and Cardboard Industry Within the paper production process, a differentiation can be made between four fields of application, namely surface, coating, mass and spraying. The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

2.2 Adhesive Industry

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textiles and Textile Care Products

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

2.4 Building Industry

Furthermore, starch may be used as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

2.5 Ground Stabilization

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

2.6 Use in Plant Protectives and Fertilizers

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

2.7 Drugs, Medicine and Cosmetics Industry

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

2.8 Starch as an Additive in Coal and Briquettes

The use of starch as an additive in coal and briquettes is also thinkable. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, the starch is suitable as a binding agent since adding it to coal and briquette can considerably reduce the emission of toxic substances.

2.9 Processing of Ore and Coal Slurry

Furthermore, the starch may be used as a flocculant in the processing of ore and coal slurry.

2.10 Additive for Casing Materials

Another field of application is the use as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfill more prerequisites for the production process, such as dispersability in cold water, rehydratisability, good mixability in sand and high capability of binding water.

2.11 Rubber Industry

In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

2.12 Production of Leather Substitutes

Another field of application for the modified starch is the production of leather substitutes.

2.13 Starch in Synthetic Polymers

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed.

One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved anti-block behavior as well as improved printability with aqueous dyes.

Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. These super absorbers are used mainly in the hygiene field, e.g. in products such as diapers and sheets, as well as in the agricultural sector, e.g. in seed pellets.

What is decisive for the use of the novel starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

What is decisive for the use of the novel starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

The production of modified starch by genetically operating with a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of the quality for certain of the above-described fields of application. These chemical modifications are principally known to the person skilled in the art. These are particularly modifications by means of heat treatment
acid treatment
oxidation and
esterification
leading to the formation of phosphate, nitrate, sulfate, xanthate, acetate and citrate starches. Other organic acids may also be used for the esterification:
formation of starch ethers
    starch alkyl ether, O-allyl ether, hydroxylalkyl ether, O-carboxylmethyl ether, N-containing starch ethers, P-containing starch ethers and S-containing starch ethers.
formation of branched starches
formation of starch graft polymers.

Furthermore, the present invention relates to the use of the nucleic acid molecules of the invention for producing plants synthesizing an amylopectin starch with a modified degree of branching in comparison to wildtype plants.

A further subject matter of the present invention is the use of the nucleic acid molecules of the invention or parts thereof or, as the case may be, of the reverse complements thereof in order to identify and isolate from plants or other organisms homologous molecules encoding proteins with the enzymatic activity of a debranching enzyme or fragments of such proteins. For the term "homology", please refer to the above definition.

In principle, the nucleic acid molecules of the invention may also be used in order to produce plants in which the activity of the debranching enzyme of the invention is increased or reduced and in which at the same time the activities of other enzymes involved in the starch biosynthesis are modified. In this regard, all kinds of combinations and permutations are conceivable. For example, nucleic acid molecules encoding a protein of the invention, or corresponding antisense- constructs may be introduced into plant cells in which the synthesis of endogeneous debranching enzymes, GBSS I-, SSS I-, II- or GBSS II-proteins is already inhibited due to an antisense-effect or a mutation, or in which the synthesis of the branching enzyme is inhibited (as described e.g. WO92/14827 or in connection with the ae mutant of maize (Shannon and Garwood, 1984, in Whistler, BeMiller and Paschall, Starch: Chemistry and Technology, Academic Press, London, $2^{nd}$ edition (1984) 25–86)).

If the inhibition of the synthesis of several debranching enzymes in transformed plants is to be achieved, DNA molecules can be used for transformation, which at the same time contain several regions in antisense-orientation encoding the respective debranching enzymes and which are controlled by a suitable promoter. In such constructs, each sequence may alternatively be controlled by its own promoter or else the sequences may be transcribed as a fusion from a common promoter. The last alternative will generally be preferred as in this case the synthesis of the respective proteins should be inhibited to approximately the same extent.

Furthermore, it is possible to construct molecules in which, apart from sequences encoding debranching enzymes, other DNA sequences are present encoding other proteins involved in the starch synthesis or modification. These are linked in antisense orientation to a suitable promoter. Again, the sequences may be connected up in series and be transcribed from a common promoter or each may be transcribed by a promoter of its own. For the length of the coding regions used in such a construct the same applies as already set forth above for the antisense constructs. There is no upper limit for the number of antisense fragments transcribed from one promoter in such a DNA molecule. The resulting transcript, however, should usually not be longer than 20 kb, preferably not longer than 5 kb. Coding regions which are located in antisense orientation downstream of a suitable promoter in such DNA molecules in combination with other coding regions may be derived from DNA sequences encoding the following proteins: granule-bound starch synthases (GBSS I and II), and soluble starch synthases (e.g. SSS I and II), branching enzymes, other debranching enzymes, disproportionizing enzymes and starch phosphorylases. This enumeration merely serves as an example. The use of other DNA sequences within the framework of such a combination is also conceivable.

By means of such constructs it is possible to inhibit the synthesis of several enzymes at the same time within the plant cells transformed with these constructs. Furthermore, the constructs may be introduced into classical mutants which are defective for one or more genes of the starch biosynthesis. These defects may be related to the following proteins: granule-bound (GBSS I and II) and soluble starch synthases (e.g. SSS I and II), branching enzymes (BE I and II), debranching enzymes, disproportionizing enzymes and starch phosphorylases. Again, this enumeration merely serves as an example.

In order to prepare the introduction of foreign genes into higher plants a high number of cloning vectors are at disposal, containing a replication signal for *E.coli* and a marker gene for the selection of transformed bacterial cells. Examples for such vectors are pBR322, pUC series, M13mp series, pACYC184 etc. The desired sequence may be integrated into the vector at a suitable restriction site. The obtained plasmid is used for the transformation of *E.coli* cells. Transformed *E.coli* cells are cultivated in a suitable medium and subsequently harvested and lysed. The plasmid is recovered. As an analyzing method for the characterization of the obtained plasmid DNA use is generally made of restriction analysis, gel electrophoresis and other biochemico-molecularbiological methods. After each manipulation the plasmid DNA may be cleaved and the obtained DNA fragments may be linked to other DNA sequences. Each plasmid DNA may be cloned into the same or in other plasmids.

In order to introduce DNA into a plant host cell a wide range of techniques are at disposal. These techniques comprise the transformation of plant cells with T-DNA by using *Agrobacterium tumefaciens* or *Agrobacterium rhizogenes* as transformation medium, the fusion of protoplasts, the injection and the electroporation of DNA, the introduction of DNA by means of the biolistic method as well as further possibilities. In the case of injection and electroporation of DNA into plant cells, there are no special demands made to the plasmids used. Simple plasmids such as pUC derivatives may be used. However, in case that whole plants are to be regenerated from cells transformed in such a way, a selectable marker gene should preferably be present.

Depending on the method of introducing desired genes into the plant cell, further DNA sequences may be necessary. If the Ti- or Ri-plasmid is used e.g. for the transformation of the plant cell, at least the right border, more preferably, however, the right and left border of the Ti- and Ri-plasmid T-DNA should be connected to the foreign gene to be introduced as a flanking region.

If Agrobacteria are used for the transformation, the DNA which is to be integrated should be cloned into special plasmids, namely either into an intermediate vector or into a binary vector. Due to sequences homologous to the sequences within the T-DNA, the intermediate vectors may be integrated into the Ti- or Ri-plasmid of the Agrobacterium due to homologous recombination. This also contains the vir-region necessary for the transfer of the T-DNA. Intermediate vectors cannot replicate in Agrobacteria. By means of a helper plasmid the intermediate vector may be transferred to *Agrobacterium tumefaciens* (conjugation). Binary vectors may replicate in *E.coli* as well as in Agrobacteria. They contain a selectable marker gene as well as a linker or polylinker which is framed by the right and the left T-DNA border region. They may be transformed directly into the Agrobacteria (Holsters et al. Mol. Gen. Genet. 163 (1978), 181–187). The Agrobacterium acting as host cell should contain a plasmid carrying a vir-region. The vir-region is necessary for the transfer of the T-DNA into the plant cell. Additional T-DNA may be present. The Agrobacterium transformed in such a way is used for the transformation of plant cells.

The use of T-DNA for the transformation of plant cells was investigated intensely and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287.

For transferring the DNA into the plant cells, plant explants may suitably be co-cultivated with *Agrobacterium tumefaciens* or *Agrobacterium rhizogenes*. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the introduced DNA is present or not. Other possibilities in order to introduce foreign DNA by using the biolistic method or by transforming protoplasts are known to the skilled person (cf. e.g. Willmitzer, L., 1993 Transgenic plants. In: Biotechnology, A Multi-Volume Comprehensive Treatise (H. J. Rehm, G. Reed, A. PUhler, P. Stadler, editors), Vol. 2, 627–659, VCH Weinheim-New York-Basel-Cambridge).

Whereas the transformation of dicotyledonous plants via Ti-plasmid vector systems by means of *Agrobacterium tumefaciens* is well established, more recent studies indicate that also monocotyledonous plants may be suitable for the transformation by means of vectors based on Agrobacterium (Chan et al., Plant Mol. Biol. 22 (1993), 491–506; Hiei et al., Plant J. 6 (1994), 271–282, Deng et al., Science in China 33 (1990), 28–34; Wilmink et al, Plant Cell Reports 11 (1992), 76–80; May et al., Bio/Technology 13 (1995), 486–492; Conner and Domisse; Int. J. Plant Sci. 153 (1992), 550–555; Ritchie et al., Transgenic Res. 2 (1993), 252–265).

Alternative Systems for the transformation of monocotyledonous plants are the transformation by means of a biolistic approach (Wan and Lemaux, Plant Physiol. 104 (1994), 37–48; Vasil et al., Bio/Technology 11 (1993), 1553–1558; Ritala et al., Plant Mol. Biol. 24 (1994), 317–325; Spencer et al., Theor. Appl. Gent. 79 (1990), 625–631), protoplast transformation, the electroporation of partially permeabilized cells, the introduction of DNA by means of glass fibers.

There are various references in the relevant literature dealing specifically with the transformation of maize (cf. e.g. WO95/06128, EP 0 513 849; EP 0 465 875; Fromm et al., Biotechnology 8 (1990), 833–844; Gordon-Kamm et al., Plant Cell 2 (1990), 603–618; Koziel et al., Biotechnology 11 (1993), 194–200). In EP 292 435 a method is described by means of which fertile plants may be obtained starting from mucousless, friable granulous maize callus. In this context it was furthermore observed by Shillito et al. (Bio/Technology 7 (1989), 581) that for regenerating fertile plants it is necessary to start from callus-suspension cultures from which a culture of dividing protoplasts can be produced which is capable to regenerate to plants. After an in vitro cultivation period of 7 to 8 months Shillito et al. obtain plants with viable descendants which, however, exhibited abnormalities in morphology and reproductivity.

Prioli and Söndahl (Bio/Technology 7 (1989), 589) have described how to regenerate and to obtain fertile plants from maize protoplasts of the Cateto maize inbreed line Cat 100-1. The authors assume that the regeneration of protoplast to fertile plants depends on a number of various factors such as the genotype, the physiological state of the donor-cell and the cultivation conditions. The successful transformation of other cereals has by now also been described, such as for barley (Wan and Lemaux, loc. cit.; Ritala et al., loc. cit.) and for wheat (Nehra et al., Plant J. 5 (1994), 285–297).

Once the introduced DNA has been integrated in the genome of the plant cell, it usually continues to be stable there and also remains within the descendants of the originally transformed cell. It usually contains a selectable marker which confers resistance against biozides or against an antibiotic such as kanamycin, G 418, bleomycin, hygromycin or phosphinotricine etc. to the transformed plant cells. The individually selected marker should therefore allow for a selection of transformed cells against cells lacking the introduced DNA.

The transformed cells grow in the usual way within the plant (see also McCormick et al., Plant Cell Reports 5 (1986), 81–84). The resulting plants can be cultivated in the usual way and cross-bred with plants having the same transformed genetic heritage or another genetic heritage. The resulting hybrid individuals have the corresponding phenotypic properties. Seeds may be obtained from the plant cells.

Two or more generations should be grown in order to ensure whether the phenotypic feature is kept stably and whether it is transferred. Furthermore, seeds should be harvested in order to ensure that the corresponding phenotype or other properties will remain.

The examples illustrate the invention.

In the examples the following methods were used.
1. Cloning Methods
   For cloning in E.coli the vector pBluescript II SK (Stratagene) was used.
2. Bacterial Strains
   For the Bluescript vector and for the pUSP constructs use was made of the E.coli strain DH5α (Bethesda Research Laboratories, Gaithersburgh, USA). The E.coli strain XL1 -Blue was used for in vivo excision.
3. Radioactive Labeling of DNA Fragments
   The radioactive labeling of DNA fragments was carried out by means of a DNA-Random Primer Labeling Kits by Boehringer (Germany) according to the manufacturer's instructions.

EXAMPLE 1

Cloning of a cDNA Encoding a Novel Debranching Enzyme from Solanum Tuberosum

In order to isolate cDNA molecules encoding a novel debranching enzyme from Solanum tuberosum, a cDNA library was constructed within the vector Lambda ZAPII (Stratagene) starting from polyA$^+$ RNA from tuber material and packed into phage heads. E.coli cells of the XL1 Blue strain were subsequently infected with the phages containing the cDNA fragments ($1 \times 10^6$ pfu) and plated on medium in Petri dishes with a densitiy of approximately 30,000 per 75 cm$^2$. After an 8-hour incubation, nitrocellulose membranes were put on the lysed bacteria and removed after one minute. The filters were first incubated in 0.5 M NaOH; 1.5 M NaCl for 2 minutes and then in 0.5 M Tris/HCl pH 7.0 for 2 minutes and finally in 2×SSC for 2 minutes. After drying and fixing the DNA by means of UV crosslinking, the filters were incubated in hybridization buffer for 3 hours at 48° C. before a radioactively labeled probe was added.

As a probe, use was made of a cDNA from maize encoding a debranching enzyme (see James et al., Plant Cell 7 (1995), 417–429, nucleotide 1150–2128).

The hybridization was carried out in 2×SSC, 10×Dehnhardt's solution; 50 mM Na$_2$HPO$_4$, pH 7.2; 0.2% SDS; 5 mM EDTA and 250 pg/ml denatured herring sperm DNA at 48° C.

Hybridizing phage clones were singled out and further purified by means of standard methods. By means of in vivo excision E.coli clones were obtained from positive phage clones. The E.coli clones contained a double-stranded pBluescript plasmid with the respective cDNA insertions. After examining the size and the restriction pattern of the insertion, plasmid DNA was isolated from suitable clones. Iso5, a plasmid isolated in such a way, contained an insertion of 2295 bp.

EXAMPLE 2

Sequence Analysis of the cDNA Insert of the Plasmid Iso5

In the case of the plasmid Iso5, which was isolated as described in Example 1, the nucleotide sequence of the cDNA insert was determined in a standard routine by means of the didesoxynucleotide-method (Sanger et al., Proc. Natl. Acad. Sci. USA 74 (1977), 5463–5467). The insert has a length of 2295 bp. The nucleotide sequence of 2133 bp of this insert and the derived amino acid sequence are indicated under Seq ID No. 1.

Homology comparisons showed that the encoded protein was a novel debranching enzyme from potato.

The nucleotide sequence depicted under SEQ ID No. 1 represents a partial cDNA encoding a so far unknown debranching enzyme from potato. By means of this sequence it is possible to isolate a complete cDNA sequence or a genomic sequence from suitable cDNA or genomic libraries by means of standard techniques.

We claim:

1. An isolated nucleic acid molecule comprising a nucleic acid sequence encoding a protein with the enzymatic activity of a debranching enzyme, wherein the nucleic acid sequence is selected from the group consisting of (a) a nucleic acid sequence encoding a protein comprising the amino acid sequence of SEQ ID NO: 2;

(b) a nucleic acid sequence that is SEQ ID NO: 1;

(c) a nucleic acid sequence that has at least 80% sequence identity to the coding region of (a) or (b);

(d) a fragment of the nucleic acid sequence of (a), (b) or (c) wherein the fragment encodes a protein which has the enzymatic activity of a debranching enzyme: and (e) a nucleic acid sequence that is degenerate as a result of the genetic code to the nucleic acid sequence of (a), (b), (c) or (d).

2. The isolated nucleic acid molecule according to claim 1, wherein the nucleic acid molecule is a cDNA molecule.

3. The isolated nucleic acid molecule according to claim 1, wherein the nucleic acid sequence has more than 90% sequence identity to the coding region of SEQ ID NO:1.

4. The isolated nucleic acid molecule according to claim 1, wherein the nucleic acid sequence has more than 95% sequence identity to the coding region of SEQ ID NO:1.

5. The isolated nucleic acid molecule according to claim 1, wherein the nucleic acid sequence is the coding region of SEQ ID NO: 1.

6. The isolated nucleic acid molecule according to claim 1, wherein the nucleic acid sequence encodes a protein comprising the amino acid sequence of SEQ ID NO: 2.

7. The isolated nucleic acid molecule according to claim 1, wherein the nucleic acid molecule is an RNA molecule.

8. A vector comprising the nucleic acid molecule according to any one of claims 1, 2, or 3–7.

9. The vector according to claim 8, wherein said nucleic acid molecule is linked in sense-orientation to regulatory elements that enable the transcription and translation of said nucleic acid molecule in prokaryotic or eukaryotic cells.

10. A host cell genetically modified with the nucleic acid molecule according to any one of claims 1, 2, or 3–7 or with a vector comprising said nucleic acid molecule, wherein said vector optionally comprises regulatory elements that enable the transcription and translation of said nucleic acid molecule in prokaryotic or eukaryotic cells.

11. A method for producing a protein with the enzymatic activity of a debranching enzyme comprising the steps of cultivating the host cell according to claim 10 under suitable conditions and recovering the synthesized protein from the culture.

12. A transgenic plant cell comprising a heterologous nucleic acid molecule according to any one of claims 1, 2, or 3–7 or comprising a vector comprising said nucleic acid molecule, wherein said nucleic acid molecule is integrated into the genome and is expressed by the transgenic plant cell.

13. A transgenic plant comprising the transgenic plant cell according to claim 12.

14. The transgenic plant according to claim 13, wherein the plant is a starch-storing plant.

15. The transgenic plant according to claim 14, wherein the plant is selected from the group consisting of cereals, legumninosae, potatoes and cassava.

16. The transgenic plant according to claim 14, wherein the plant is a potato plant.

17. A propagation material of a transgenic plant comprising the transgenic plant cell according to claim 12.

18. An isolated nucleic acid molecule comprising a nucleic acid sequence, wherein said isolated nucleic acid molecule, when introduced into a plant cell, has a cosuppression effect on the expression of a debranching enzyme, wherein the nucleic acid sequence is selected from the group consisting of:

(a) a nucleic acid sequence encoding a protein comprising the amino acid sequence of SEQ ID NO 2;

(b) a nucleic acid sequence that is the coding region of SEQ ID NO: 1;

(c) a nucleic acid sequence that has at least 80% sequence identity to (a) or (b);

(d) a part of the nucleic acid sequence of (a), (b) or (c), wherein the part is sufficient to reduce the activity of debranching enzyme; and (e) the complementary strand of the nucleic acid sequence of (a), (b), (c) or (d).

19. A transgenic plant cell that exhibits a reduced activity of a debranching enzyme, when compared to an untransformed plant cell, and wherein the transgenic plant cell comprises a recombinant molecule integrated into its genome, wherein said recombinant molecule comprises (a) a promoter active in plant cells; and (b) a nucleic acid molecule comprising a nucleic acid sequence according to claim 18 or 23, that leads to a cosuppression effect in said plant cell.

20. A transgenic plant comprising the plant cell according to claim 19.

21. The transgenic plant according to claim 20, wherein the plant is a potato plant.

22. A propagation material of a transgenic plant comprising the transgenic plant cell according to claim 19.

23. The isolated nucleic acid molecule of claim 7, wherein the nucleic acid sequence has greater than 95% sequence identity to the coding region of SEQ ID NO: 1.

24. A vector comprising the nucleic acid molecule according to claim 18 or 23.

25. A host cell genetically modified with the nucleic acid molecule according to claim 18 or 23 or with a vector comprising said nucleic acid molecule.

26. A transgenic plant cell that exhibits increased activity of a debranching enzyme when compared to untransformed cells, and wherein the transgenic plant cell comprises a recombinant molecule integrated into its genome, wherein said recombinant molecule comprises:

a) a promotor active in plant cells;

b) the nucleic acid molecule according to any one of claims 1, 2, or 3–7, wherein the nucleic acid molecule is linked to the promotor in sense-orientation; and c) optionally, a termination signal for the termination of transcription and the addition of a poly-A tail to the developing transcript.

27. A transgenic plant comprising the plant cell according to claim 26.

28. A propagation material of the transgenic plant according to claim 27.

* * * * *

SEQUENCE LISTING

<160> NUMBER OF SEQ ID NOS: 2

<210> SEQ ID NO: 1
<211> LENGTH: 2133
<212> TYPE: DNA
<213> ORGANISM: Solanum tuberosum
<220> FEATURE:
<221> NAME/KEY: CDS
<222> LOCATION: (2)..(1819)
<223> OTHER INFORMATION: Clone: Iso5

<400> SEQUENCE: 1

```
g aat tcg gca cga ggg cca gag gat gat tgt tgg ccc cca atg gca ggc      49
  Asn Ser Ala Arg Gly Pro Glu Asp Asp Cys Trp Pro Pro Met Ala Gly
   1               5                  10                  15 atg gta cct tct gct tct gat cag ttt gat tgg gaa gga gat cta tta       97
Met Val Pro Ser Ala Ser Asp Gln Phe Asp Trp Glu Gly Asp Leu Leu
                 20                  25                  30 ctg aag ttt cca cag aga gat ctt gta atc tat gaa atg cat gtt cgt      145
Leu Lys Phe Pro Gln Arg Asp Leu Val Ile Tyr Glu Met His Val Arg
         35                  40                  45 gga ttt aca aat cat gag tcg agt gaa aca aaa tat cct ggt act tac      193
Gly Phe Thr Asn His Glu Ser Ser Glu Thr Lys Tyr Pro Gly Thr Tyr
     50                  55                  60 ctt ggt gtt gtg gag aaa ctt gat cac ttg aag gaa ctt ggt gtc aac      241
Leu Gly Val Val Glu Lys Leu Asp His Leu Lys Glu Leu Gly Val Asn
 65                  70                  75                  80 tgt ata gag cta atg ccc tgt cac gag ttc aat gag ctg gag tac tat      289
Cys Ile Glu Leu Met Pro Cys His Glu Phe Asn Glu Leu Glu Tyr Tyr
                 85                  90                  95 agt tat aac tct gta ttg ggc gac tac aag ttt aac ttt tgg ggc tat      337
Ser Tyr Asn Ser Val Leu Gly Asp Tyr Lys Phe Asn Phe Trp Gly Tyr
                100                 105                 110 tct act gtc aat ttc ttt tct cca atg gga aga tac tcg tct gct ggt      385
Ser Thr Val Asn Phe Phe Ser Pro Met Gly Arg Tyr Ser Ser Ala Gly
            115                 120                 125 cta agt aat tgc ggc ctc ggt gca ata aac gaa ttt aag tat ctt gtc      433
Leu Ser Asn Cys Gly Leu Gly Ala Ile Asn Glu Phe Lys Tyr Leu Val
        130                 135                 140 aag gaa gca cat aaa cgt gga atc gag gtt atc atg gat gtt gtt ttc      481
Lys Glu Ala His Lys Arg Gly Ile Glu Val Ile Met Asp Val Val Phe
145                 150                 155                 160 aat cac act gct gaa gga aat gaa aat ggt ccc ata cta tca ttt aga      529
Asn His Thr Ala Glu Gly Asn Glu Asn Gly Pro Ile Leu Ser Phe Arg
                165                 170                 175 ggc att gac aac agt gtg ttt tat acg cta gct cct aag ggt gaa ttt      577
Gly Ile Asp Asn Ser Val Phe Tyr Thr Leu Ala Pro Lys Gly Glu Phe
            180                 185                 190 tac aac tac tca gga tgt gga aat acc ttc aac tgt aat aat ccc att      625
Tyr Asn Tyr Ser Gly Cys Gly Asn Thr Phe Asn Cys Asn Asn Pro Ile
        195                 200                 205 gta cgt caa ttt ata gtg gat tgc ttg aga tat tgg gtt acc gaa atg      673
Val Arg Gln Phe Ile Val Asp Cys Leu Arg Tyr Trp Val Thr Glu Met
    210                 215                 220 cac gta gat ggc ttc cgc ttt gat ctt gct tct atc ctt aca aga agt      721
His Val Asp Gly Phe Arg Phe Asp Leu Ala Ser Ile Leu Thr Arg Ser
225                 230                 235                 240 agc agc tcg tgg aat gct gta aat gtc tat gga aat tca att gac ggt      769
Ser Ser Ser Trp Asn Ala Val Asn Val Tyr Gly Asn Ser Ile Asp Gly
                245                 250                 255
```

```
gac atg atc acc aca ggc act cct ctc aca agc cca cca ttg att gat     817
Asp Met Ile Thr Thr Gly Thr Pro Leu Thr Ser Pro Pro Leu Ile Asp
        260                 265                 270 atg att agc aat gat cca ata ctt agt gga gta aag ctt ata gct gaa     865
Met Ile Ser Asn Asp Pro Ile Leu Ser Gly Val Lys Leu Ile Ala Glu
        275                 280                 285 gca tgg gat tgt gga ggc ctt tac caa gtt ggc atg ttt ccg cac tgg     913
Ala Trp Asp Cys Gly Gly Leu Tyr Gln Val Gly Met Phe Pro His Trp
        290                 295                 300 ggt atc tgg tcg gag tgg aac gga aag tac cgt gac atg gta cgt cag     961
Gly Ile Trp Ser Glu Trp Asn Gly Lys Tyr Arg Asp Met Val Arg Gln
305                 310                 315                 320 ttc atc aaa ggc act gat ggg ttt tct ggg gct ttt gct gaa tgc ctt    1009
Phe Ile Lys Gly Thr Asp Gly Phe Ser Gly Ala Phe Ala Glu Cys Leu
            325                 330                 335 tgt gga agc cca aat cta tac cag aaa gga gga aga aaa cca tgg aac    1057
Cys Gly Ser Pro Asn Leu Tyr Gln Lys Gly Gly Arg Lys Pro Trp Asn
            340                 345                 350 agt ata aat ttc gtg tgt gcc cac gat ggt ttt act ttg gct gat tta    1105
Ser Ile Asn Phe Val Cys Ala His Asp Gly Phe Thr Leu Ala Asp Leu
            355                 360                 365 gtg aca tac aac aat aaa cac aat ttg gca aat gga gag gac aac aaa    1153
Val Thr Tyr Asn Asn Lys His Asn Leu Ala Asn Gly Glu Asp Asn Lys
370                 375                 380 gat ggg gag aat cac aat aat agt tgg aat tgt ggc gag gaa gga gaa    1201
Asp Gly Glu Asn His Asn Asn Ser Trp Asn Cys Gly Glu Glu Gly Glu
385                 390                 395                 400 ttt gca agt atc ttt gtg aag aaa ttg agg aaa aga caa atg cgg aac    1249
Phe Ala Ser Ile Phe Val Lys Lys Leu Arg Lys Arg Gln Met Arg Asn
            405                 410                 415 ttc ttc ctc tgc ctt atg gtt tcc caa ggt gtt ccc atg ata tat atg    1297
Phe Phe Leu Cys Leu Met Val Ser Gln Gly Val Pro Met Ile Tyr Met
            420                 425                 430 ggt gat gaa tat ggt cac act aag gga gga aac aac aac acg tat tgc    1345
Gly Asp Glu Tyr Gly His Thr Lys Gly Gly Asn Asn Asn Thr Tyr Cys
            435                 440                 445 cat gac aat tat att aat tac ttc cgt tgg gat aag aag gat gaa tct    1393
His Asp Asn Tyr Ile Asn Tyr Phe Arg Trp Asp Lys Lys Asp Glu Ser
450                 455                 460 tca tct gat ttt ttg aga ttt tgc ggc ctc atg acc aaa ttc cgc cat    1441
Ser Ser Asp Phe Leu Arg Phe Cys Gly Leu Met Thr Lys Phe Arg His
465                 470                 475                 480 gaa tgt gaa tca ctg gga tta gat ggt ttc cct aca gca gaa agg ctg    1489
Glu Cys Glu Ser Leu Gly Leu Asp Gly Phe Pro Thr Ala Glu Arg Leu
            485                 490                 495 caa tgg cat ggt cac act cct aga act cca gat tgg tct gaa aca agt    1537
Gln Trp His Gly His Thr Pro Arg Thr Pro Asp Trp Ser Glu Thr Ser
            500                 505                 510 cga ttc gtt gca ttt aca ctg gtc gac aaa gtg aag gga gaa cta tat    1585
Arg Phe Val Ala Phe Thr Leu Val Asp Lys Val Lys Gly Glu Leu Tyr
            515                 520                 525 att gcc ttt aac gcc agc cat ttg cct gta acg att aca ctt cca gaa    1633
Ile Ala Phe Asn Ala Ser His Leu Pro Val Thr Ile Thr Leu Pro Glu
530                 535                 540 aag cct ggt tat aga tgg cag ccg ttt gtg gac aca ggc aaa cca gca    1681
Lys Pro Gly Tyr Arg Trp Gln Pro Phe Val Asp Thr Gly Lys Pro Ala
545                 550                 555                 560 cca ttt gac ttc ctg aca gac gat gtt cct gag aga gag aca gca gcc    1729
Pro Phe Asp Phe Leu Thr Asp Asp Val Pro Glu Arg Glu Thr Ala Ala
```

-continued

```
            565                 570                 575
aaa caa tat tct cat ttt ctg gac gcg aac cag tat ccg atg ctc agt    1777
Lys Gln Tyr Ser His Phe Leu Asp Ala Asn Gln Tyr Pro Met Leu Ser
            580                 585                 590 tat tca tcc att att ctt tta cta tca tct gct gat gat gcg            1819
Tyr Ser Ser Ile Ile Leu Leu Leu Ser Ser Ala Asp Asp Ala
            595                 600             605 tagtttcatt caacaagcca ggtgaggtaa agcagcttca gattttgtta tatgcagtga  1879
ggtgttactt tgtaaataaa gtaagaaaca ggacagaaca gaactgcaaa cagatagaac  1939
tggtgaggaa gaagctgatg atttataaga tacaccttgt attataattg tatttatata  1999
aaataaaaaa aaaaaactag tgaacttgtc tgtgcgaaat aaaatgtata gttgatttca  2059
aaaaaaaaaa aaaaaaaaaa aaaaaactc gagctctctc tctctctctc tctctctctc  2119
tctctctctc tctc                                                    2133

<210> SEQ ID NO: 2
<211> LENGTH: 606
<212> TYPE: PRT
<213> ORGANISM: Solanum tuberosum

<400> SEQUENCE: 2

Asn Ser Ala Arg Gly Pro Glu Asp Asp Cys Trp Pro Pro Met Ala Gly
 1               5                  10                  15

Met Val Pro Ser Ala Ser Asp Gln Phe Asp Trp Glu Gly Asp Leu Leu
                20                  25                  30

Leu Lys Phe Pro Gln Arg Asp Leu Val Ile Tyr Glu Met His Val Arg
            35                  40                  45

Gly Phe Thr Asn His Glu Ser Ser Glu Thr Lys Tyr Pro Gly Thr Tyr
        50                  55                  60

Leu Gly Val Val Glu Lys Leu Asp His Leu Lys Glu Leu Gly Val Asn
    65                  70                  75                  80

Cys Ile Glu Leu Met Pro Cys His Glu Phe Asn Glu Leu Glu Tyr Tyr
                85                  90                  95

Ser Tyr Asn Ser Val Leu Gly Asp Tyr Lys Phe Asn Phe Trp Gly Tyr
                100                 105                 110

Ser Thr Val Asn Phe Phe Ser Pro Met Gly Arg Tyr Ser Ser Ala Gly
            115                 120                 125

Leu Ser Asn Cys Gly Leu Gly Ala Ile Asn Glu Phe Lys Tyr Leu Val
        130                 135                 140

Lys Glu Ala His Lys Arg Gly Ile Glu Val Ile Met Asp Val Val Phe
145                 150                 155                 160

Asn His Thr Ala Glu Gly Asn Glu Asn Gly Pro Ile Leu Ser Phe Arg
                165                 170                 175

Gly Ile Asp Asn Ser Val Phe Tyr Thr Leu Ala Pro Lys Gly Glu Phe
            180                 185                 190

Tyr Asn Tyr Ser Gly Cys Gly Asn Thr Phe Asn Cys Asn Asn Pro Ile
        195                 200                 205

Val Arg Gln Phe Ile Val Asp Cys Leu Arg Tyr Trp Val Thr Glu Met
    210                 215                 220

His Val Asp Gly Phe Arg Phe Asp Leu Ala Ser Ile Leu Thr Arg Ser
225                 230                 235                 240

Ser Ser Ser Trp Asn Ala Val Asn Val Tyr Gly Asn Ser Ile Asp Gly
                245                 250                 255

Asp Met Ile Thr Thr Gly Thr Pro Leu Thr Ser Pro Pro Leu Ile Asp
```

-continued

```
                    260                     265                      270
Met Ile Ser Asn Asp Pro Ile Leu Ser Gly Val Lys Leu Ile Ala Glu
                275                     280                     285
Ala Trp Asp Cys Gly Gly Leu Tyr Gln Val Gly Met Phe Pro His Trp
        290                     295                     300
Gly Ile Trp Ser Glu Trp Asn Gly Lys Tyr Arg Asp Met Val Arg Gln
305                     310                     315                     320
Phe Ile Lys Gly Thr Asp Gly Phe Ser Gly Ala Phe Ala Glu Cys Leu
                    325                     330                     335
Cys Gly Ser Pro Asn Leu Tyr Gln Lys Gly Gly Arg Lys Pro Trp Asn
                340                     345                     350
Ser Ile Asn Phe Val Cys Ala His Asp Gly Phe Thr Leu Ala Asp Leu
                355                     360                     365
Val Thr Tyr Asn Asn Lys His Asn Leu Ala Asn Gly Glu Asp Asn Lys
            370                     375                     380
Asp Gly Glu Asn His Asn Asn Ser Trp Asn Cys Gly Glu Glu Gly Glu
385                     390                     395                     400
Phe Ala Ser Ile Phe Val Lys Lys Leu Arg Lys Arg Gln Met Arg Asn
                    405                     410                     415
Phe Phe Leu Cys Leu Met Val Ser Gln Gly Val Pro Met Ile Tyr Met
                420                     425                     430
Gly Asp Glu Tyr Gly His Thr Lys Gly Gly Asn Asn Asn Thr Tyr Cys
                435                     440                     445
His Asp Asn Tyr Ile Asn Tyr Phe Arg Trp Asp Lys Lys Asp Glu Ser
        450                     455                     460
Ser Ser Asp Phe Leu Arg Phe Cys Gly Leu Met Thr Lys Phe Arg His
465                     470                     475                     480
Glu Cys Glu Ser Leu Gly Leu Asp Gly Phe Pro Thr Ala Glu Arg Leu
                    485                     490                     495
Gln Trp His Gly His Thr Pro Arg Thr Pro Asp Trp Ser Glu Thr Ser
                500                     505                     510
Arg Phe Val Ala Phe Thr Leu Val Asp Lys Val Lys Gly Glu Leu Tyr
            515                     520                     525
Ile Ala Phe Asn Ala Ser His Leu Pro Val Thr Ile Thr Leu Pro Glu
        530                     535                     540
Lys Pro Gly Tyr Arg Trp Gln Pro Phe Val Asp Thr Gly Lys Pro Ala
545                     550                     555                     560
Pro Phe Asp Phe Leu Thr Asp Asp Val Pro Glu Arg Glu Thr Ala Ala
                    565                     570                     575
Lys Gln Tyr Ser His Phe Leu Asp Ala Asn Gln Tyr Pro Met Leu Ser
                580                     585                     590
Tyr Ser Ser Ile Ile Leu Leu Leu Ser Ser Ala Asp Asp Ala
                595                     600                     605
```